United States Patent
Morgan et al.

(10) Patent No.: US 8,170,690 B2
(45) Date of Patent: May 1, 2012

(54) IMPLANTABLE MEDICAL LEAD HAVING AN ANCHOR PROVIDING ENHANCED FIXATION

(75) Inventors: Kevin L. Morgan, Simi Valley, CA (US); Phong D. Doan, Stevenson Ranch, CA (US); Conor Flannery, Santa Monica, CA (US)

(73) Assignee: Pacesetter, Inc., Sylmar, CA (US)

( * ) Notice: Subject to any disclaimer, the term of this patent is extended or adjusted under 35 U.S.C. 154(b) by 561 days.

(21) Appl. No.: 12/370,985

(22) Filed: Feb. 13, 2009

(65) Prior Publication Data

US 2010/0211149 A1   Aug. 19, 2010

(51) Int. Cl.
*A61N 1/05* (2006.01)

(52) U.S. Cl. ........ 607/127; 607/116; 607/126; 607/130; 607/131

(58) Field of Classification Search ........... 607/127, 607/131, 116, 126, 130; 600/375
See application file for complete search history.

(56) References Cited

U.S. PATENT DOCUMENTS

| | | | |
|---|---|---|---|
| 5,002,067 A * | 3/1991 | Berthelsen et al. | 607/120 |
| 6,078,840 A * | 6/2000 | Stokes | 607/127 |
| 7,126,451 B2 * | 10/2006 | Maruyama | 336/200 |
| 7,197,362 B2 * | 3/2007 | Westlund | 607/127 |
| 7,212,870 B1 | 5/2007 | Helland | |
| 7,448,644 B2 * | 11/2008 | Zhong et al. | 280/729 |
| 2007/0123967 A1 | 5/2007 | Barlov et al. | |
| 2008/0109054 A1 * | 5/2008 | Hastings et al. | 607/127 |
| 2009/0171425 A1 * | 7/2009 | Dahlberg | 607/127 |
| 2009/0281608 A1 * | 11/2009 | Foster | 607/127 |
| 2010/0211149 A1 * | 8/2010 | Morgan et al. | 607/127 |

* cited by examiner

*Primary Examiner* — Niketa Patel
*Assistant Examiner* — Joseph Stoklosa (57) ABSTRACT

An implantable medical lead is disclosed herein wherein the lead employs a helical distal tip anchor having improved fixation capabilities. The implantable medical lead may include a body and a helical anchor. The body may include a distal end and a proximal end. The helical anchor may be at least one of extending and extendable from the distal end. The helical anchor may include at least one loop including first and second straight sides that intersect at a first corner.

7 Claims, 6 Drawing Sheets

IMPLANTABLE MEDICAL LEAD HAVING AN ANCHOR PROVIDING ENHANCED FIXATION

FIELD OF THE INVENTION

The present invention relates to medical apparatus and methods. More specifically, the present invention relates to implantable medical leads and methods of manufacturing such leads.

BACKGROUND OF THE INVENTION

Active fixation leads, such as screw-in type leads, typically employ a helical anchor that is extendable from the distal tip of the lead and can be screwed into cardiac tissue to affix the lead distal tip to the cardiac tissue. In addition to serving as an anchor, a helical anchor may also act as a tip electrode for pacing and/or sensing.

Screw-in type helical anchors are made of a smooth biocompatible wire shaped into the form of a helix. The surface of the helical anchor may have a microscopic coating of titanium nitride, which is used for electrical enhancement, but does not provide a mechanical lock to secure the helical anchor in cardiac tissue.

Since the surface of the helical anchor is relatively smooth, there is no mechanical interlock between the helical anchor surface and cardiac tissue once the helical anchor is fixated into cardiac tissue. The helical anchor is free to rotate out of the cardiac tissue in which the helical anchor is imbedded if external forces are significant enough to cause rotation of the helical anchor. Therefore, if any rotation of a lead body or lead inner coil of an extendable/retractable screw-in type lead occurs during the acute phase post implant (e.g., between zero and one to two weeks), the helical anchor has a high probability of unscrewing from the cardiac tissue. The result of the unscrewing may be lead to dislodgment and loss of capture and sensing capabilities. These results could place the patient in a medical emergency depending on the condition of the patient.

There is a need in the art for a helical anchor configuration that enhances the fixation of the helical anchor to the cardiac tissue, thereby reducing the likelihood of dislodgement, loss of capture and loss of sensing.

SUMMARY

An implantable medical lead is disclosed herein. In one embodiment, the lead includes a body and a helical anchor. The body may include a distal end and a proximal end. The helical anchor may be at least one of extending and extendable from the distal end. The helical anchor may include at least one loop including first and second straight sides that intersect at a first corner.

Another implantable medical lead is disclosed herein. In one embodiment, the lead includes a body and a helical anchor. The body may include a distal end and a proximal end. The helical anchor may be at least one of extending and extendable from the distal end. The helical anchor may include at least one loop radially extending about, and generally transverse to, a longitudinal axis of the body. The at least one loop may include multiple straight segments.

Yet another implantable medical lead is disclosed herein. In one embodiment, the lead includes a body and a helical anchor. The body may include a distal end and a proximal end. The helical anchor may be at least one of extending and extendable from the distal end. The helical anchor may include at least one loop radially extending about, and generally transverse to, a longitudinal axis of the body. The at least one loop may include multiple corners. The corners by generally be oriented to point radially outward relative to the longitudinal axis.

Another implantable medical lead is disclosed herein. In one embodiment, the lead includes a body and a helical anchor. The body may include a distal end and a proximal end. The helical anchor may be at least one of extending and extendable from the distal end. The helical anchor may include at least one loop radially extending about, and generally transverse to, a longitudinal axis of the body. The at least one loop may form a geometrical shape having multiple straight sides and multiple corners. The geometrical shape may be at least one of a triangle, a square, a pentagon and a hexagon.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

An implantable medical lead 10 is disclosed herein wherein the lead 10 employs a helical distal tip anchor 77 having improved fixation capabilities. In one embodiment, the lead 10 includes a body 50 and a helical anchor 77. The body 50 may include a distal end 45 and a proximal end 40. The helical anchor 77 may be at least one of extending and extendable from the distal end 45. The helical anchor 77 may include at least one loop 210 radially extending about, and generally transverse to, a longitudinal axis of the body 50. The at least one loop 210 may form a geometrical shape having multiple straight sides 230 and multiple corners 225. The geometrical shape may be at least one of a triangle, a square, a pentagon and a hexagon. The geometrical shape, or more specifically, the shape's sides 230 and corners 225 may create pressure points along the helical anchor 77 when imbedded in cardiac tissue. The pressure points resist the tendency of the helical anchor 77 to inadvertently rotate out of the tissue. Thus, the geometric shape of the helical anchor 77 may for a mechanical interlock with the cardiac tissue in which it is imbedded. While the pressure points substantially increase the resistance to inadvertent rotation of the helical anchor out of the tissue, the mechanical interlock is not so great as to substantially increase the difficulty associated with purposely rotating the helical anchor out of the tissue to allow the lead to be extracted from the patient.

Figure 1:
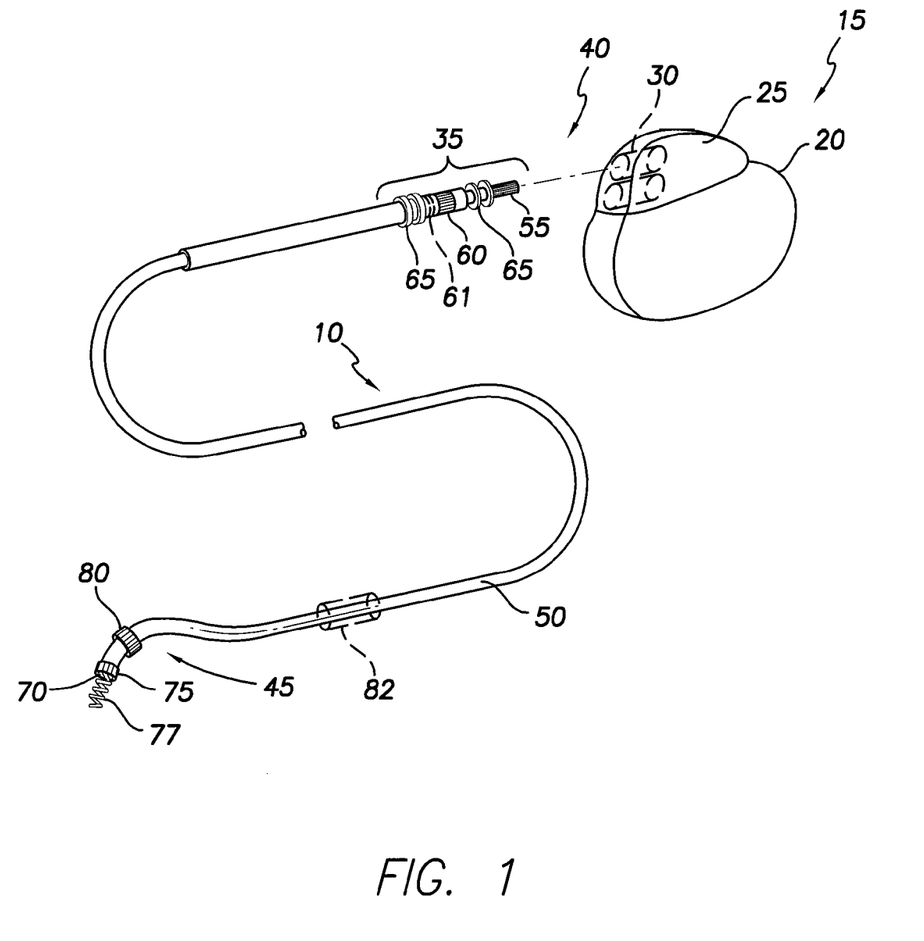
FIG. 1 is an isometric view of an implantable medical lead and a pulse generator for connection thereto.

For a general discussion of an embodiment of a lead 10 employing the helical anchor 77 disclosed herein, reference is made to FIG. 1, which is an isometric view of the implantable medical lead 10 and a pulse generator 15 for connection thereto. The pulse generator 15 may be a pacemaker, defibrillator, ICD or neurostimulator. As indicated in FIG.1, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIG. 1, in one embodiment, the lead 10 may include a proximal end 40, a distal end 45 and a tubular body 50 extending between the proximal and distal ends. In some embodiments, the lead may be a 6 French, model 1688T lead, as manufactured by St. Jude Medical of St. Paul, Minn. In other embodiments, the lead may be a 6 French model 1346T lead, as manufactured by St. Jude Medical of St. Paul, Minn. In other embodiments, the lead 10 may be of other sizes and models. The lead 10 may be configured for a variety of uses. For example, the lead 10 may be a RA lead, RV lead, LV Brady lead, RV Tachy lead, intrapericardial lead, etc.

As indicated in FIG. 1, the proximal end 40 may include a lead connector end 35 including a pin contact 55, a first ring contact 60, a second ring contact 61, which is optional, and sets of spaced-apart radially projecting seals 65. In some embodiments, the lead connector end 35 may include the same or different seals and may include a greater or lesser number of contacts. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

As illustrated in FIG. 1, in one embodiment, the lead distal end 45 may include a distal tip 70, a tip electrode 75, a ring electrode 80, and the helical anchor 77. In some embodiments where the helical anchor 77 only acts as a fixation device, the tip electrode 75 may be in the form of a ring or domed cap at the distal tip 70 of the lead body 50 and is held against the cardiac tissue when the helical anchor 77 is fully imbedded in the cardiac tissue.

Figure 2:
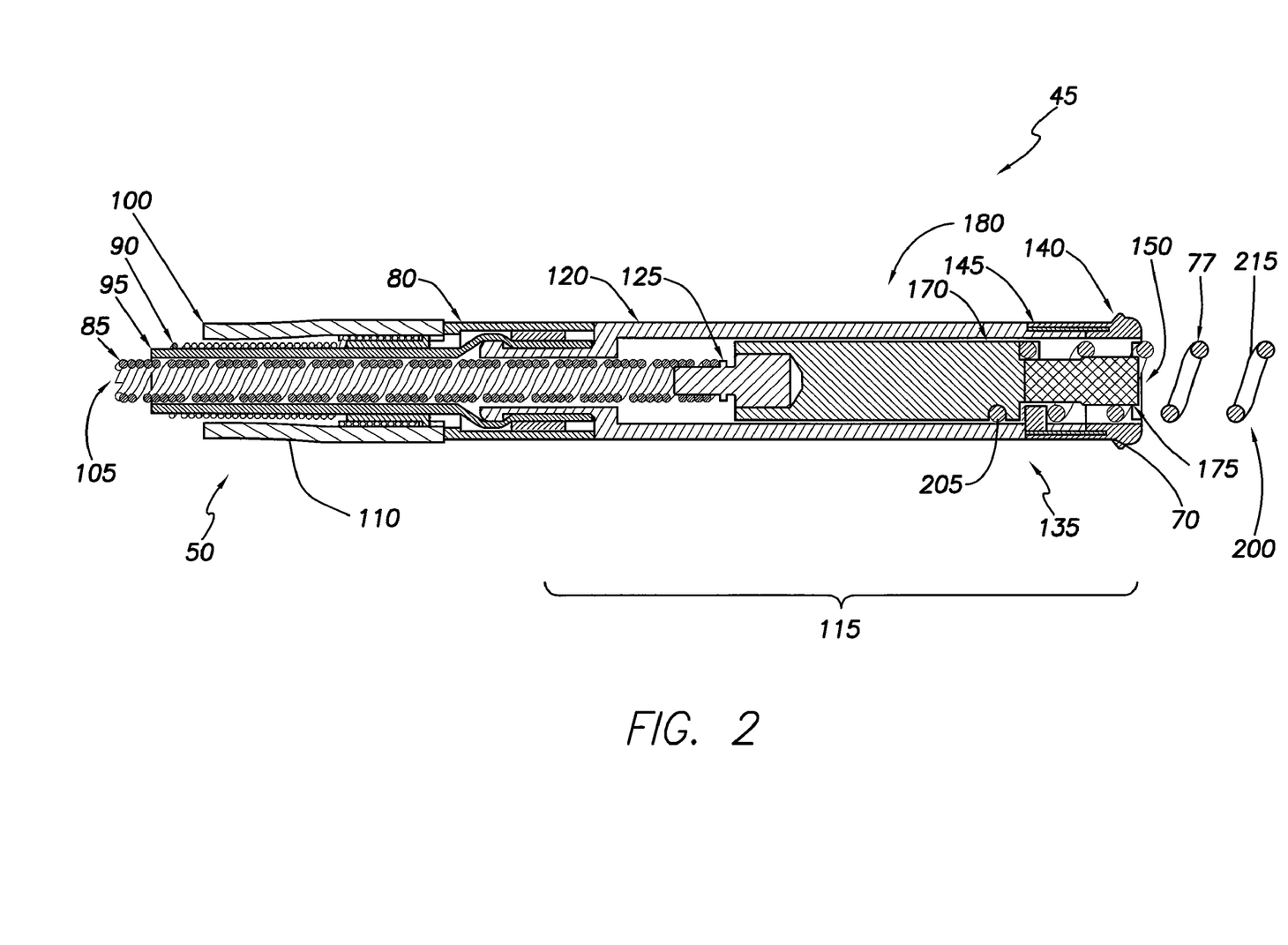
FIG. 2 is a longitudinal cross-section of the lead distal end.

In some embodiments, the helical anchor 77 may also serve as the tip electrode of the lead 10 such that lead 10 does not include the ring or domed cap tip electrode depicted in FIG. 1. Such an embodiment is depicted in FIG. 2, which is a longitudinal cross-section of the lead distal end 45 with the helical anchor 77 also serving as a tip electrode. As indicated in FIG. 2, the tip electrode 77 may be in the form of a helical anchor 77 that is extendable from within the distal tip 70 for active fixation and serving as a tip electrode 77.

As shown in FIG. 1, in some embodiments, the distal end 45 may include a defibrillation coil 82 about the outer circumference of the lead body 50. The defibrillation coil 82 may be located proximal of the distal tip 70.

The ring electrode 80 may extend about the outer circumference of the lead body 50, proximal of the distal tip 70. In other embodiments, the distal end 45 may include a greater or lesser number of electrodes 75, 80 in different or similar configurations.

As can be understood from FIGS. 1 and 2, in one embodiment, the tip electrode 75 or 77 may be in electrical communication with the pin contact 55 via a first electrical conductor 85, and the ring electrode 80 may be in electrical communication with the first ring contact 60 via a second electrical conductor 90. In some embodiments, the defibrillation coil 82 may be in electrical communication with the second ring contact 61 via a third electrical conductor. In yet other embodiments, other lead components (e.g., additional ring electrodes, various types of sensors, etc.) (not shown) mounted on the lead body distal region 45 or other locations on the lead body 50 may be in electrical communication with a third ring contact (not shown) similar to the second ring contact 61 via a fourth electrical conductor (not shown). Depending on the embodiment, any one or more of the conductors 85, 90 may be a multi-strand or multi-filar cable or a single solid wire conductor run singly or grouped, for example in a pair.

As shown in FIG. 2, in one embodiment, the lead body 50 proximal of the ring electrode 80 may have a concentric layer configuration and may be formed at least in part by inner and outer helical coil conductors 85, 90, an inner tubing 95, and an outer tubing 100. The helical coil conductor 85, 90, the inner tubing 95 and the outer tubing 100 form concentric layers of the lead body 50. The inner helical coil conductor 85 forms the inner most layer of the lead body 50 and defines a central lumen 105 for receiving a stylet or guidewire therethrough. The inner helical coil conductor 85 is surrounded by the inner tubing 95 and forms the second most inner layer of the lead body 50. The outer helical coil conductor 90 surrounds the inner tubing 95 and forms the third most inner layer of the lead body 50. The outer tubing 100 surrounds the outer helical coil conductor 90 and forms the outer most layer of the lead body 50.

In one embodiment, the inner tubing 95 may be formed of an electrical insulation material such as, for example, ethylene tetrafluoroethylene ("ETFE"), polytetrafluoroethylene ("PTFE"), silicone rubber, silicone rubber polyurethane copolymer ("SPC"), or etc. The inner tubing 95 may serve to electrically isolate the inner conductor 85 from the outer conductor 90. The outer tubing 100 may be formed of a biocompatible electrical insulation material such as, for example, silicone rubber, SPC, polyurethane, gore, or etc. The outer tubing 100 may serve as the jacket 100 of the lead body 50, defining the outer circumferential surface 110 of the lead body 50.

As illustrated in FIG. 2, in one embodiment, the lead body 50 in the vicinity of the ring electrode 80 transitions from the above-described concentric layer configuration to a header assembly 115. For example, in one embodiment, the outer tubing 100 terminates at a proximal edge of the ring electrode 80, the outer conductor 90 mechanically and electrically couples to a proximal end of the ring electrode 80, the inner tubing 95 is sandwiched between the interior of the ring electrode 80 and an exterior of a proximal end portion of a body 120 of the header assembly 115, and the inner conductor 85 extends distally past the ring electrode 80 to electrically and mechanically couple to components of the header assembly 115 as discussed below.

As depicted in FIG. 2, in one embodiment, the header assembly 115 may include the body 120, a coupler 125, and a helix assembly 135. The header body 120 may be a tube forming the outer circumferential surface of the header assembly 115 and enclosing the components of the assembly 115. The header body 120 may have a soft atraumatic distal tip 140 with a radiopaque marker 145 to facilitate the soft atraumatic distal tip 140 being visualized during fluoroscopy. The distal tip 140 may form the extreme distal end 70 of the lead 10 and includes a distal opening 150 through which the helical anchor 77 may be extended or retracted. The header body 120 may be formed of polyetheretherketone ("PEEK"), polyurethane, or etc., the soft distal tip 140 may be formed of silicone rubber, SPC, or etc., and the radiopaque marker 145 may be formed of platinum, platinum-iridium alloy, tungsten, tantalum, or etc.

As shown in FIG. 2, a proximal portion of the coupler 125 may be received in the lumen 105 of the inner coil conductor 85 at the extreme distal end of the inner coil conductor 85, the inner coil conductor 85 and the coupler 125 being mechanically and electrically coupled to each other. The coupler 125 may be formed of MP35N, platinum, platinum iridium alloy, stainless steel, or etc.

As indicated in FIG. 2, the helix assembly 135 may include a base 170, the helical anchor electrode 77, and a steroid plug 175. The base 170 forms the proximal portion of the assembly 135. The helical anchor electrode 77 forms the distal portion of the assembly 135. The steroid plug 175 may be located within the volume defined by the helical coils of the helical anchor electrode 77. The base 170 and the helical anchor electrode 77 are mechanically and electrically coupled together. The distal portion of the coupler 125 may be received in the helix base 170 such that the coupler 125 and the helix base 170 are mechanically and electrically coupled to each other. The base 170 of the helix assembly 135 may be formed of platinum, platinum-iridium alloy, MP35N, stainless steel, or etc. The helical anchor electrode 77 may be formed of platinum, platinum-iridium ally, MP35N, stainless steel, or etc.

As can be understood from FIG. 2 and the preceding discussion, the coupler 125 and helix assembly 135 are mechanically coupled together such that these elements 125, 170, 135 of the header assembly 115 do not displace relative to each other. Instead these elements 125, 135 of the header assembly 115 are capable of displacing as a unit relative to, and within, the body 120 when a stylet or similar tool is inserted through the lumen 105 to engage the coupler 125. In other words, these elements 125, 135 of the header assembly 115 form an electrode assembly 180, which can be caused to displace relative to, and within, the header assembly body 120 when a stylet engages the proximal end of the coupler 125. Specifically, the stylet is inserted into the lumen 105 to engage the coupler 125, wherein rotation of the electrode assembly 180 via rotating the stylet or the inner coil 85 in a first direction causes the electrode assembly 180 to displace distally, and rotation of the electrode assembly 180 via rotating the stylet or the inner coil 85 in a second direction causes the electrode assembly 180 to retract into the header assembly body 120. Thus, causing the electrode assembly 180 to rotate within the body 120 in a first direction causes the helical anchor electrode 77 to emanate from the tip opening 150 for screwing into tissue at the implant site. Conversely, causing the electrode assembly 180 to rotate within the body 120 in a second direction causes the helical anchor electrode 77 to retract into the tip opening 150 to unscrew the anchor 77 from the tissue at the implant site.

As already mentioned and indicated in FIG. 2, the proximal end of the coupler 125 is electrically coupled to the distal end of the inner coil conductor 85, and the distal end of the coupler 125 is electrically coupled to the helix base 170, which is electrically coupled to the helical anchor 77. Thus, in one embodiment, the coupler 125 and helix base 170 form an electrical pathway through the header assembly 115 from the inner coil conductor 85 to the helical anchor 77.

Figure 3:
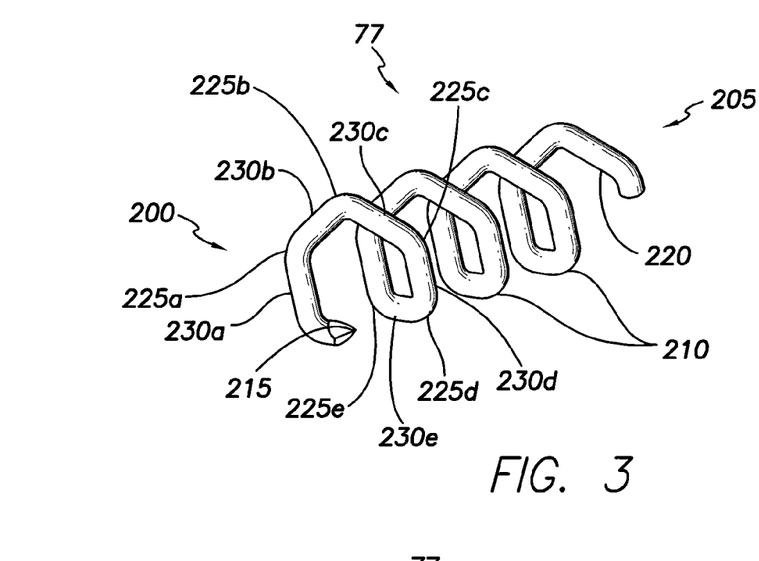
FIG. 3 is an isometric view of a first embodiment of the helical anchor.
Figure 4:
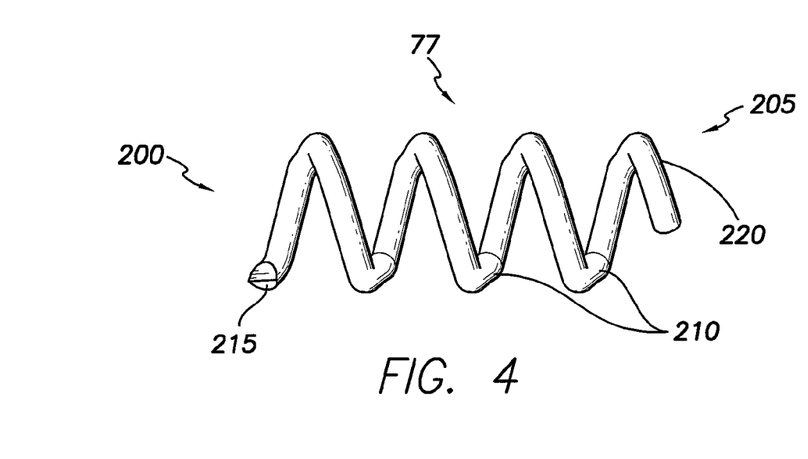
FIG. 4 is a side view of the first embodiment of the helical anchor.
Figure 5:
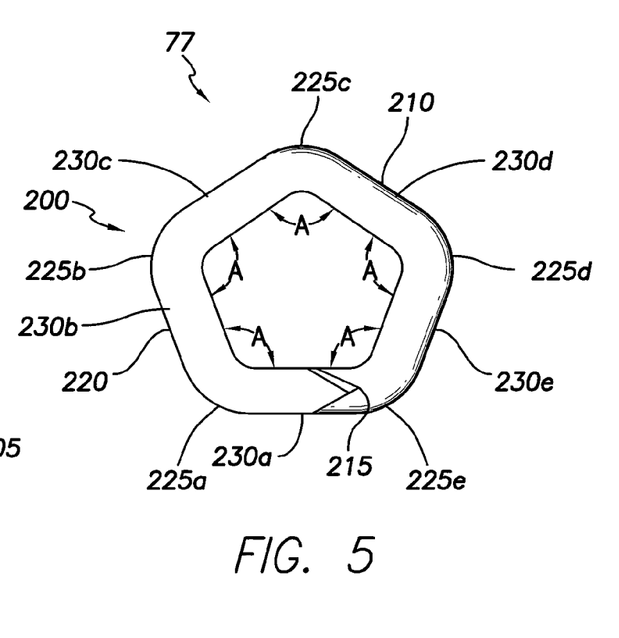
FIG. 5 is an end view of the first embodiment of the helical anchor.

For a detailed discussion of the features of a first embodiment of the helical anchor 77, reference is made to FIGS. 3-5, which are, respectively, isometric, side and end views of the first embodiment of the helical anchor 77. As shown in FIGS. 3 and 4, the helical anchor 77 may include a distal end 200, a proximal end 205, a plurality of loops or coils 210, and a distal point 215. As can be understood from FIG. 2, the proximal end 205 mechanically and electrically couples to the helix base 170, and the distal point 215 is sharp and positioned such that the point 215 will pierce cardiac tissue when the helical anchor 77 is rotated in the correct direction.

As indicated in FIG. 5, in one embodiment, the helical anchor 77 is configured such that its coils 210, when viewed in a direction extending along the longitudinal axis of the helical anchor 77, form a pentagon shape. In one embodiment, each pentagon-shaped complete loop 210 of the wire 220 forming the helical anchor 77 will have a regular pentagon shape and include five equal straight sides 230a-230e, five corners 225a-225e, and five equal inner angles A of 108 degrees. Thus, as indicated in FIG. 5, the first and second sides 230a, 230b intersect at a first corner 225a, the second and third sides 230b, 230c intersect at a second corner 225b, the third and fourth sides 230c, 230d intersect at a third corner 225c, the fourth and fifth sides 230d, 230e intersect at a fourth corner 225d, and the fifth and first 230e, 230a sides intersect at a fifth corner 225e.

In other embodiments, each pentagon-shaped complete loop 210 of the wire 220 forming the helical anchor 77 will generally approximate a pentagon shape and include five straight sides 230a-230e that may be approximately equal, five corners 225a-225e, and five inner angles A of approximately 108 degrees. Thus, in some embodiments, the loop 210 may be shaped as a regular pentagon.

Figures 6, 7:
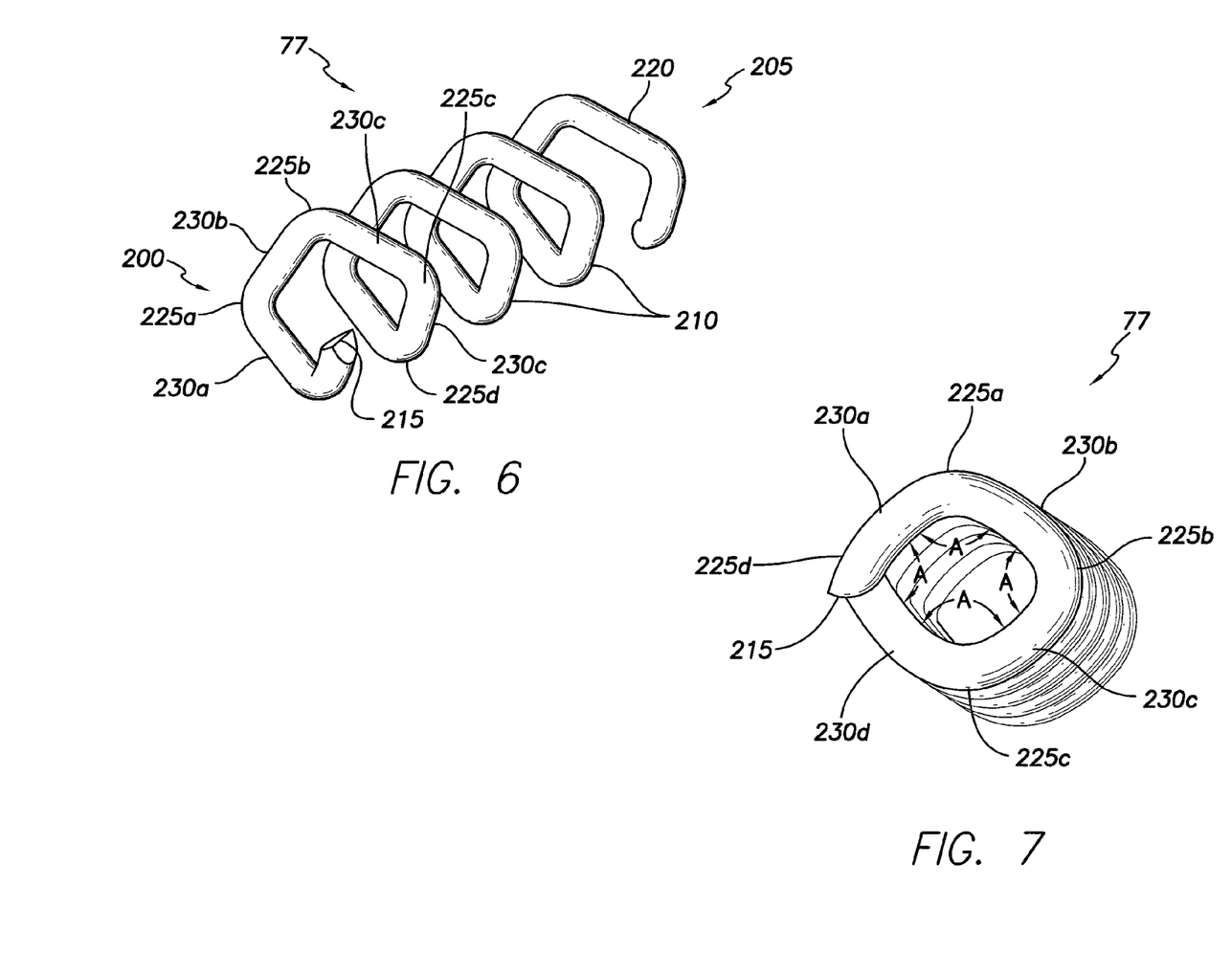
FIG. 6 is an isometric view of a second embodiment of the helical anchor.
FIG. 7 is an end view of the second embodiment of the helical anchor.

For a detailed discussion of the features of a second embodiment of the helical anchor 77, reference is made to FIGS. 6 and 7, which are, respectively, isometric and end views of the second embodiment of the helical anchor 77. As shown in FIGS. 6 and 7, the helical anchor 77 may include a distal end 200, a proximal end 205, a plurality of loops or coils 210, and a distal point 215. As can be understood from FIG. 2, the proximal end 205 mechanically and electrically couples to the helix base 170, and the distal point 215 is sharp and positioned such that the point 215 will pierce cardiac tissue when the helical anchor 77 is rotated in the correct direction.

As indicated in FIG. 7, in one embodiment, the helical anchor 77 is configured such that its coils 210, when viewed in a direction extending along the longitudinal axis of the helical anchor 77, form a square shape. In one embodiment, each square-shaped complete loop 210 of the wire 220 forming the helical anchor 77 will have a square shape and include four equal straight sides 230a-230d, four corners 225a-225d, and four equal inner angles A of 90 degrees. Thus, as indicated in FIG. 7, the first and second sides 230a, 230b intersect at a first corner 225a, the second and third sides 230b, 230c intersect at a second corner 225b, the third and fourth sides 230c, 230d intersect at a third corner 225c, and the fourth and first sides 230d, 230a intersect at a fourth corner 225d.

In other embodiments, each square-shaped complete loop 210 of the wire 220 forming the helical anchor 77 will generally approximate a square shape and include four straight sides that may be approximately equal, four corners 225a-225d, and four inner angles A of approximately 90 degrees. Thus, in some embodiments, the loop 210 may be shaped as a square, although in other embodiments, the loop 210 may be shaped as another type of four sided shape, such as a rectangle or trapezoid.

Figure 8:
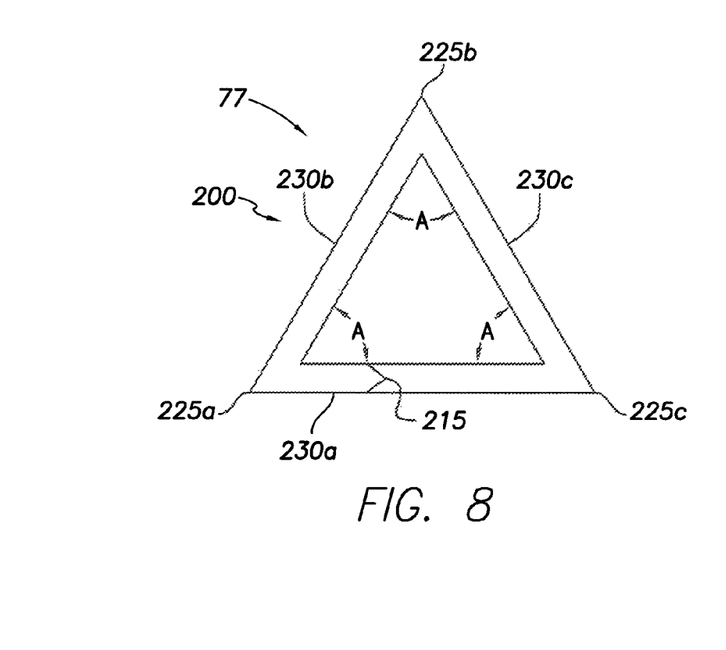
FIG. 8 is an end view of a third embodiment of the helical anchor.

For a detailed discussion of the features of a third embodiment of the helical anchor 77, reference is made to FIG. 8 which is an end view of the third embodiment of the helical anchor 77. As with the first and second embodiments discussed with respect to FIGS. 3-7 and as can be understood from FIG. 8, the helical anchor 77 of the third embodiment may include a distal end 200, a proximal end 205, a plurality of loops or coils 210, and a distal point 215. As can be understood from FIG. 2, the proximal end 205 mechanically and electrically couples to the helix base 170, and the distal point 215 is sharp and positioned such that the point 215 will pierce cardiac tissue when the helical anchor 77 is rotated in the correct direction.

As indicated in FIG. 8, in one embodiment, the helical anchor 77 is configured such that its coils 210, when viewed in a direction extending along the longitudinal axis of the helical anchor 77, form a triangular shape. In one embodiment, each triangular-shaped complete loop 210 of the wire 220 forming the helical anchor 77 will have a triangular shape and include three equal straight sides 230a-230c, three corners 225a-225c, and three equal inner angles A of 60 degrees. Thus, as indicated in FIG. 8, the first and second sides 230a, 230b intersect at a first corner 225a, the second and third sides 230b, 230c intersect at a second corner 225b, and the third and first sides 230c, 230a intersect at a third corner 225c.

In other embodiments, each triangular-shaped complete loop 210 of the wire 220 forming the helical anchor 77 will generally approximate a triangle shape and include three straight sides 230a-230c that may be approximately equal, three corners 225a-225c, and three inner angles A of approximately 60 degrees. Thus, in some embodiments, the loop 210 may be shaped as an equilateral triangle.

Figure 9:
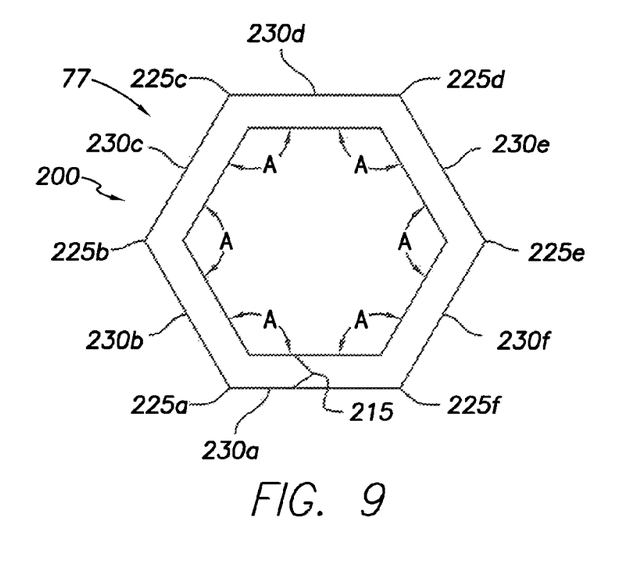
FIG. 9 is an end view of a fourth embodiment of the helical anchor.

For a detailed discussion of the features of a fourth embodiment of the helical anchor 77, reference is made to FIG. 9 which is an end view of the fourth embodiment of the helical anchor 77. As with the first and second embodiments discussed with respect to FIGS. 3-7 and as can be understood from FIG. 9, the helical anchor 77 of the fourth embodiment may include a distal end 200, a proximal end 205, a plurality of loops or coils 210, and a distal point 215. As can be understood from FIG. 2, the proximal end 205 mechanically and electrically couples to the helix base 170, and the distal point 215 is sharp and positioned such that the point 215 will pierce cardiac tissue when the helical anchor 77 is rotated in the correct direction.

As indicated in FIG. 9, in one embodiment, the helical anchor 77 is configured such that its coils 210, when viewed in a direction extending along the longitudinal axis of the helical anchor 77, form a hexagonal shape. In one embodiment, each hexagonal-shaped complete loop 210 of the wire 220 forming the helical anchor 77 will have a hexagonal shape and include six equal straight sides 230a-230f, six corners 225a-225f, and six equal inner angles A of 120 degrees. Thus, as indicated in FIG. 9, the first and second sides 230a, 230b intersect at a first corner 225a, the second and third sides 230b, 230c intersect at a second corner 225b, the third and fourth sides 230c, 230d intersect at a third corner 225c, the fourth and fifth sides 230d, 230e intersect at a fourth corner 225d, the fifth and sixth sides 230e, 230f intersect at a fifth corner 225e, and the sixth and first sides 230f, 230a intersect at a sixth corner 225f. scribbled In other embodiments, each hexagonal-shaped complete loop 210 of the wire 220 forming the helical anchor 77 will generally approximate a hexagon shape and include six straight sides 230a-230f that may be approximately equal, six corners 225a-225f, and six inner angles A of approximately 120 degrees. Thus, in some embodiments, the loop 210 may be shaped as a regular hexagon.

As can be understood from FIGS. 3-9, because the helical anchors 77 of the various embodiments have loops 210 that are geometrically shaped as triangles, squares, pentagons or hexagons, the loops 210 each have multiple straight segments 230 and corners 225. Loops 210 so configured, or more specifically, the straight segments 230 and corners 225, create pressure points along the helical anchor 77 that resist the tendency of the helical anchor 77 to rotate out of the tissue. Thus, the straight segments 230 and corners 225 of the loops 210 create a mechanical interlock due to interaction of the features 225, 230 of the loops 210 with the tissue elasticity. Thus, the features 230, 225 of the loops 210 substantially reduce the likelihood that the helical anchor 77 will inadvertently rotate out of the tissue during the acute phase of implantation. However, because of the subtleness of the features, the enhanced fixation of the helical anchor 77 afforded by the features 230, 225 does not cause a problem with respect to chronic fixation, thereby allowing the helical anchor 77 to be intentionally extracted from the cardiac tissue in which it is imbedded. Accordingly, the features 230, 225 and overall configuration of the helical anchor 77 provide substantially improved fixation with respect to inadvertent disengagement of the helical anchor 77 from the cardiac tissue that is not too excessive to present problems with respect to intentional anchor extraction.

The first through fourth embodiments discussed above with respect to FIGS. 3-9 increase the fixation of the helical anchor 77 over standard anchors known in the art. In some embodiments, the first and second embodiments discussed above with respect to FIGS. 3-7 may provide a unique combination of increased fixation as compared to that offered by the third and fourth embodiments discussed with respect to FIGS. 8 and 9. For example, the first and second embodiments (i.e., the pentagon and square shaped anchors) may offer increased fixation over the fourth embodiment (i.e., the hexagon shaped anchor), and the first and second embodiments may offer better intentional extractability as compared to the third embodiment (i.e., the triangle shaped anchor). Thus, the first and second embodiments may provide the best combination of fixation and ease of intentional extraction.

As can be understood from FIGS. 1 and 2, depending on the embodiment, the helical anchor 77 may be at least one of extending and extendable from the distal end 70. Also, as can be understood from the various embodiments depicted in FIGS. 3-9, the helical anchor 77 may include at least one loop 210 radially extending about, and generally transverse to, a longitudinal axis of the lead body 50, as can be understood from FIG. 2. The at least one loop 210 may include multiple corners 225, and these corners 225 may be generally oriented to point radially outward relative to the longitudinal axis.

Figure 10:
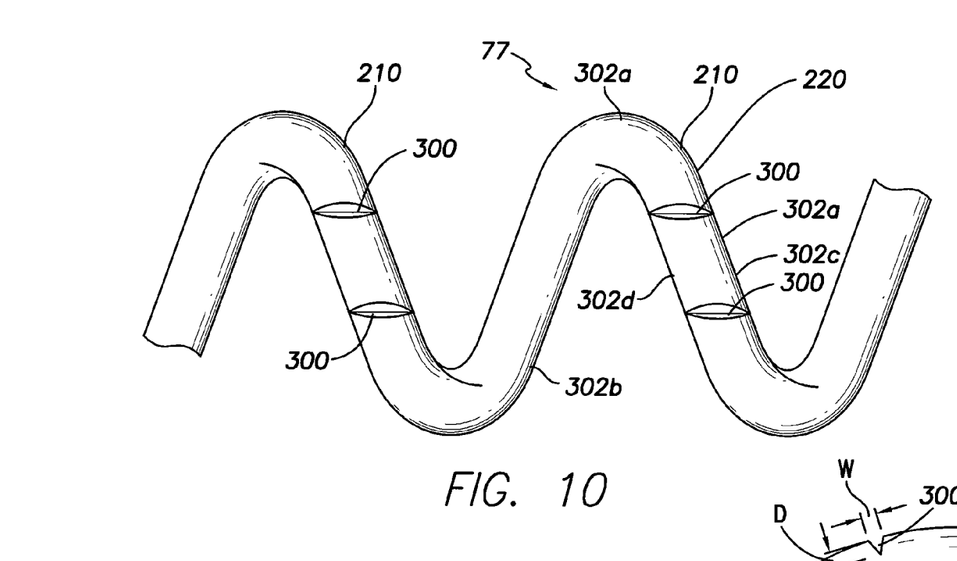
FIG. 10 is a side view of a length of a helical anchor.
Figure 11:
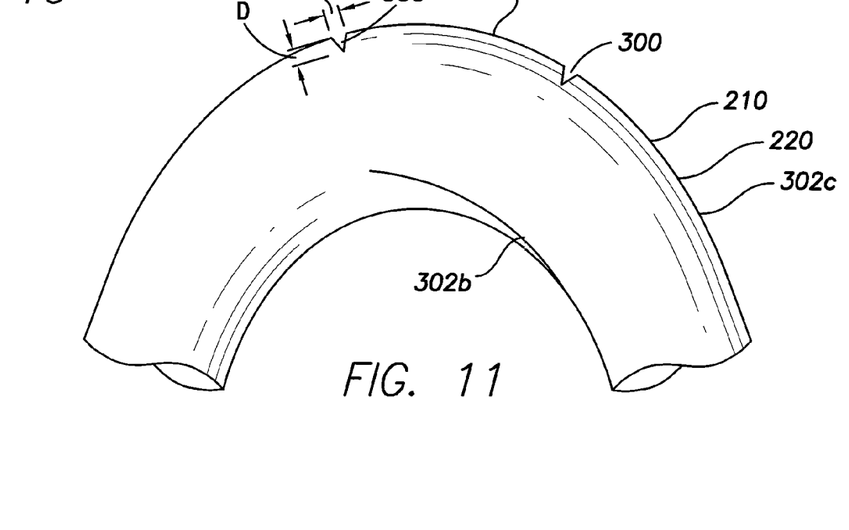
FIG. 11 is an end view of a segment of a radial length of a loop 210 of a helical anchor as if viewed from a distal or proximal end of the helical anchor.

As shown in FIGS. 10 and 11, which are, respectively, a side view of a length of a helical anchor 77 and an end view of a segment of a radial length of a loop 210 of a helical anchor 77, the wire 220 forming the helical anchor 77 may have features 300 defined in the surface 302 of the wire 220. For example, the features 300 may be notches 300 defined in the surface 302 of the wire 220. In some embodiment, the notches 300 may be defined in the outer surface 302a of the wire 220. In other embodiments, the notches 300 may be defined in the inner surface 302b of the wire 220, the proximal surface 302c of the wire 220, and/or the distal surface 302d of the wire 220, in addition to or in place of the notches 300 defined in the outer surface 302a. The notches 300 may be defined in the surface 302 of the wire 220 forming the helical anchor 77 to allow in-growth of fibrotic tissue. This in-growth within the notches 300 aids in the stabilization of the helical anchor 77. Because of the time needed for fibrosis to form within the notches 300, the fixation advantage offered by the notches 300 may facilitate chronic retention of the helical anchor 77 within the cardiac tissue.

In some embodiments, the notches 300 may be generally evenly distributed along the length of the wire 220 as a series of single notches, pairs of notches, groups of three notches, groups of four notches, etc. In other embodiments, the notches may not be evenly distributed along the length of the wire 220.

As can be understood from FIG. 11, in some embodiments, the notches 300 may have a triangular cross section defined in the wire 220 having a depth D of between approximately 0.002 inch and approximately 0.007 inch and a width W of between approximately 0.005 inch and approximately 0.016 inch. In some embodiments, the notch depth D may be between approximately five percent to approximately forty percent of the diameter of the wire 220. The notches 300 may be formed in the wire 220 via such methods as stamping, rolling, machining, etc.

Although the present invention has been described with reference to preferred embodiments, persons skilled in the art will recognize that changes may be made in form and detail without departing from the spirit and scope of the invention.

What is claimed is:

1. An implantable medical lead comprising:
    a body including a distal end and a proximal end; and
    a generally helical anchor that is at least one of extending and extendable from the distal end,
    wherein the generally helical anchor comprises at least one loop including first and second straight sides that intersect at a first corner, wherein the loop further includes third and fourth sides, the second and third sides intersecting at a second corner, the third and fourth sides intersecting at a third corner, and the fourth and first sides intersecting at a fourth corner, wherein the sides and corners of the loop cause the loop to be square-shaped.

2. An implantable medical lead comprising:
    a body including a distal end and a proximal end; and
    a helical anchor that is at least one of extending and extendable from the distal end,
    wherein the helical anchor comprises at least one loop including first and second straight sides that intersect at a first corner, and wherein the loop further includes third, fourth and fifth sides, the second and third sides intersecting at a second corner, the third and fourth sides intersecting at a third corner, the fourth and fifth sides intersecting at a fourth corner, and the fifth and first sides intersecting at a fifth corner, wherein the sides and corners of the loop cause the loop to be shaped as a regular pentagon.

3. An implantable medical lead comprising:
    a body including a distal end and a proximal end; and
    a helical anchor that is at least one of extending and extendable from the distal end,
    wherein the helical anchor comprises at least one loop including first and second straight sides that intersect at a first corner, and wherein the loop further includes third, fourth, fifth and sixth sides, the second and third sides intersecting at a second corner, the third and fourth sides intersecting at a third corner, the fourth and fifth sides intersecting at a fourth corner, the fifth and first sides intersecting at a fifth corner, and the sixth and first sides intersecting at a sixth corner, wherein the sides and corners of the loop cause the loop to be shaped as a regular hexagon.

4. An implantable medical lead comprising:
    a body including a distal end and a proximal end; and
    a helical anchor that is at least one of extending and extendable from the distal end,
    wherein the helical anchor comprises at least one loop including first and second straight sides that intersect at a first corner, and wherein the loop further includes a third side, the second and third sides intersecting at a second corner, and the third and first sides intersecting at a third corner, wherein the sides and corners of the loop cause the loop to be shaped as an equilateral triangle.

5. The implantable medical lead of claim 1, wherein a notch is defined in a surface of the at least one loop.

6. An implantable medical lead comprising:
    a body including a distal end and a proximal end; and
    a helical anchor that is at least one of extending and extendable from the distal end and comprising at least one loop radially extending about, and generally transverse to, a longitudinal axis of the body, the at least one loop forming a geometrical shape having multiple straight sides and multiple corners, wherein the geometrical shape is at least one of a triangle, a square, a pentagon and a hexagon.

7. The implantable medical lead of claim 6, wherein a notch is defined in a surface of the at least one loop.

* * * * *